US00PP19144P2

(12) United States Plant Patent
Carruth

(10) Patent No.: US PP19,144 P2
(45) Date of Patent: Aug. 26, 2008

(54) GRANDIFLORA ROSE PLANT NAMED 'WEKBEPMEY'

(50) Latin Name: *Rosa hybrida*
Varietal Denomination: WEKbepmey

(75) Inventor: Thomas F. Carruth, Altadena, CA (US)

(73) Assignee: Weeks Wholesale Rose Grower, Inc., Rancho Cucamonga, CA (US)

( * ) Notice: Subject to any disclaimer, the term of this patent is extended or adjusted under 35 U.S.C. 154(b) by 0 days.

(21) Appl. No.: 11/973,156

(22) Filed: Oct. 5, 2007

(51) Int. Cl.
*A01H 5/00* (2006.01)

(52) U.S. Cl. ..... Plt./130
(58) Field of Classification Search ..... Plt./130, Plt./134
See application file for complete search history.

*Primary Examiner*—Annette H Para
(74) *Attorney, Agent, or Firm*—Christie, Parker & Hale, LLP

(57) ABSTRACT

A new variety of Grandiflora rose suitable for garden decoration, having flowers of deep golden yellow coloration blushed with pink.

1 Drawing Sheet

Classification: The present invention relates to a new *Rosa hybrida* plant.

Variety denomination: The new plant has the varietal denomination 'WEKbepmey'.

BACKGROUND OF THE INVENTION

This invention relates to a new and distinct variety of Grandiflora Rose. It has as its seed parent the variety known as 'CHRiscinn' (not patented) and as its pollen parent the variety known as 'WEKosomit' (U.S. Plant Pat. No. 14,401).

SUMMARY OF THE INVENTION

Among the features which distinguish the new variety from other presently available and commercial rose cultivars known to the inventor are the following combination of characteristics: its red suffusion on the inner surface of the sepal that appears as the flower ages, its stipitate glands on the new shoots, its moderate tea to somewhat fruity fragrance and its red suffusion on the branches evidenced during cooler weather conditions. The plants has an upright growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKbepmey' may be asexually propagated by cuttings, budding and grafting. The budding and grafting successfully occurred on the plant/rootstock Rosa hybrida cv. 'Dr. Huey' (not patented).

COMPARISON WITH PARENTS

The new rose may be distinguished from its seed parent, 'CHRiscinn' by the following combination of characteristics: whereas 'WEKbepmey' bears medium sized flowers (about 9.1 to about 10.7 cm. in diameter) of deep golden yellow coloration blushed with pink, the seed parent bears significantly smaller flowers of pink and tan blended coloration. The new variety is classified as a grandiflora rose with an upright tall growing habit (about 160 to about 190 cm. in height), whereas 'CHRiscinn' is classified as a floribunda rose with a significantly shorter and more compact growing habit.

The new variety may be distinguished from its pollen parent, 'WEKosomit' by the following combination of characteristics: whereas 'WEKbepmey' produces medium sized flowers (about 9.1 to about 10.7 cm. in diameter) of deep golden yellow coloration blushed with pink, the pollen parent produces significantly larger flowers (about 9.7 to about 13.6 cm. in diameter) of clear pure yellow coloration. The new variety bears double flowers (about 30 to 37 petals), whereas 'WEKosomit' bears double flowers with significantly heavier petalage (about 39 to 44 petals).

COMPARISON WITH THE CLOSEST COMMERCIALLY AVAILABLE CULTIVAR

The new variety may be distinguished from its closest commercially available cultivar, 'WEKjuvoo' U.S. Plant Pat. No. 10,071 by the following combination of characteristics: whereas 'WEKbepmey' bears medium sized flowers (about 9.1 to about 10.7 cm. in diameter) of deep golden yellow coloration blushed with pink, the closest commercially available cultivar bears significantly larger flowers (about 10.5 to about 13 cm. in diameter) of bright orange-yellow coloration blushed red. The new variety is classified as a grandiflora rose with an upright tall growing habit (about 160 to about 190 cm. in height), whereas 'WEKjuvoo' is classified as a hybrid tea rose with a significantly shorter and more compact growing habit (about 120 to 155 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoor in Pomona, Calif. in the month of June. Phenotypic expression may vary with environmental, cultural and climatic conditions, as well as differences in conditions of light and soil.

FLOWER

The new variety usually bears its flowers singly, sometimes in clusters of two to four or more per stem. Flowers may be borne in regular rounded clusters on strong medium to long stems (about 26 to about 81 cm.). Outdoors, the plant blooms abundantly and nearly continuously during the growing season. The flowers have a moderate tea to somewhat fruity fragrance.

BUD

The peduncle is about 2.9 to about 6.0 cm. in length, of average to somewhat heavy caliper (about 0.3 to about 0.5 cm. in diameter), and usually erect. It is moderately smooth, with some stipitate glands. Peduncle color is between 146B and 137C often heavily suffused, especially on the side exposed to the sun, with between 187B and 187A.

Before the calyx breaks, the bud is about 1.1 to about 1.9 cm. in diameter at the widest point, about 1.8 to about 2.6 cm. in length, and pointed in shape. The surface of the bud bears few foliaceous appendages and stipitate glands, usually with slender entire foliaceous parts extending beyond the tip of the bud about ¼ or more of its length. Bud color is between 144B and 146B often moderately suffused, especially on the side exposed to the sun, with between 187A and 183A.

The sepals are about 2.4 to about 3.9 cm. in length and about 0.6 to about 1.0 cm. in width at the widest point. The outer surface color of the sepal is between 144B and 146B often moderately suffused, especially on the side exposed to the sun, with between 187A and 183A. The inner surface color of the sepal is between 137A and 139D. After the sepals open, the inner surface color is often heavily suffused, especially on the area exposed to the sun, with the between 187A and 187B. The sepals are covered with fine wooly tomentum; sepal margins are lined with some stipitate glands and numerous hairs.

The receptacle of the flower is of medium length (about 0.6 to about 0.9 cm.) and average in caliper (about 0.5 to about 0.8 cm. in diameter). The receptacle is urn-shaped in form. Its surface is very smooth with thick fleshy walls. The receptacle color is between 144A and 137C.

As the petals open (after the calyx breaks), the bud is about 2.0 to about 3.2 cm. in diameter at the widest point, about 3.2 to about 4.1 cm. in length, and pointed to somewhat ovoid in form. The color of the under surfaces of the newly opened petals is between 26A and 28C often blushed on the outermost petals and on the petal tips of the inner petals with between 53A and 53B. At the point where the petal attaches, there is a moderately large zone of between 9B and 12A. The color of the upper surfaces of the newly opened petals is between 24A and 26B. At the point where the petal attaches, there is a somewhat large zone of between 9A and 12A.

BLOOM

When fully open, the bloom ranges from about 9.1 to about 10.7 cm. in diameter. Petalage is double with about 30 to 37 petals and about 2 to 8 petaloids irregularly arranged. When partially open, the bloom form is moderately ovoid to somewhat high centered, and the petals are moderately tightly spiraled with petal edges somewhat reflexed outward. When fully open, the bloom form is very cupped, and the petals are loosely cupped with petal edges somewhat reflexed outward.

PETALS

The substance of the petals is moderately heavy and of somewhat thin to medium thickness, with upper surfaces slightly satiny and under surfaces matte to somewhat shiny. The petals are about 3.3 to about 5.6 cm. in length and about 2.5 to about 5.9 cm. in width at the widest point. Petal margins are entire.

The outer petals are nearly round in shape with rounded apices.

The inner petals are broadly oblanceolate in shape with rounded apices.

Petaloids are about 1.0 to about 2.7 cm. in length and about 0.8 to about 2.3 cm. in width at the widest point. Petaloids are irregularly shaped oblanceolate to somewhat subulate with rounded apices.

NEWLY OPENED FLOWER

The under surface color of the outer petals is between 24C and 24B often moderately blushed with between 53B and 53C. At the point where the petal attaches, there is a moderately large zone of between 9B and 12B. The upper surface color of the outer petals is between 23B and 23C sometimes lightly blushed with between 53B and 53C. At the point where the petal attaches, there is a somewhat large zone of between 9A and 12A.

The under surface color of the intermediate and inner petals is between 21D and 24B. The upper surface color of the intermediate and inner petals is between 21C and 23C.

The under and upper surface color of the petaloids are similar in coloration to the upper and under surfaces of the intermediate and inner petals.

The general tonality of the newly opened flower is between 21C and 23C.

THREE-DAY-OLD FLOWER

The under surface color of the outer petals is between 26C and 23C often moderately blushed with between 53B and 53C. At the point where the petal attaches, there is a moderately large zone of near 9C. The upper surface color of the outer petals is between 21C and 23C often moderately blushed with between 53B and 53C. At the point where the petal attaches, there is a somewhat large zone of between 9A and 12A.

The under surface color of the intermediate and inner petals is between 19B and 23C sometimes lightly blushed with between 53C and 53D. The upper surface color of the intermediate and inner petals is between 20B and 23C often moderately blushed with between 53B and 53C.

The under and upper surface color of the petaloids are similar in coloration to the upper and under surfaces of the intermediate and inner petals.

The general tonality of the three-day-old flower is between 20B and 23C often moderately blushed with between 53B and 53C.

On the spent bloom, the petals usually drop off cleanly.

In June in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 60) and are arranged regularly about the pistils; a few are mixed with petaloids. The filaments are of medium to long length (about 0.8 to about 1.5 cm.) most with anthers. Filaments are between 12A and 9A in color at the base suffusing to near 23B at the top. The anthers are moderately small for the class and all open approximately at the same time. Anther color when immature is near 22A on the external part and near 11C on the internal part. Anther color at maturity is near 165B on the external part and near 200A on the internal part. Pollen is abundant and near 16B in color.

FEMALE REPRODUCTIVE ORGANS

Pistils vary in number (average about 80). The styles are somewhat uneven, average to somewhat long in length (about 0.8 to about 1.2 cm.), moderately thin in caliper, and loosely bunched. Stigma color is between 11C and 14D. Style color is between 8C and 10C usually heavily suffused with between 53B and 53A. Ovaries are usually all enclosed in the calyx.

Hips have not been observed on this variety when grown in Pomona, Calif.

FOLIAGE

The compound leaves are usually comprised of three to seven leaflets and are borne abundantly. The five-leaflet leaves are about 8.9 to about 13.1 cm. in length and about 7.4 to about 9.2 cm. in width at the widest point, moderately thin to somewhat crisp in texture, and semi-glossy in finish. The terminal leaflets are about 4.5 to about 6.0 cm. in length and about 2.7 to about 4.2 cm. in width at the widest point, shaped ovate to somewhat oval with acuminate apices and rounded to slightly acute bases. Their margins are usually simple serraty.

The upper surface color of the mature leaf is between 137A and 146A. The under surface color of the mature leaf is between 147B and 148B. The upper surface color of the young leaf is between 146A and 148B, usually heavily suffused with between 187B and 183B. The under surface color of the young leaf is between 138B and 148B, usually heavily suffused with between 187B and 183A.

The rachis is somewhat light in caliper and moderately rough. The upper side is shallowly grooved with some hairs and stipitate glands on the edges of the grooves. The under side of the rachis is moderately rough with some stipitate glands and few small prickles. The rachis color is between 146B and 146C.

The stipules are about 1.2 to about 2.1 cm. in length and of medium width (about 0.4 to about 0.8 cm.) with medium length straight points that usually turn out at an angle of more than 45 degrees and sometimes slightly recurve toward the stem. The stipules color is between 146C and 146B.

The petiole is somewhat light in caliper and moderately rough. The upper side is shallowly grooved with some hairs and stipitate glands on the edges of the grooves. The under side of the petiole is moderately rough with some stipitate glands and few small prickles. The petiole is about 0.9 to about 1.6 cm. in length and about 0.1 to about 0.15 cm in diameter at the widest point. The petiole color is between 146B and 146C.

The plant displays an above average degree of resistance to powdery mildew and rust as compared to other commercial varieties grown under comparable conditions in Pomona, Calif. The plant's winter hardiness and drought/heat tolerance are yet to be determined.

GROWTH

The plant has an upright tall growing habit (about 160 to about 190 cm. in height and about 50 to about 65 cm. spread at the widest point), with full branching. It displays very vigorous growth and the canes are of somewhat light caliper for the class.

The color of the major stems is between 146A and 147B. They bear some large prickles that are about 0.8 to about 1.2 cm. in length. The large prickles are almost straight to slightly angled downward with a somewhat short moderately broad oval base; prickle color is between 164A and 166C. The major stem bears few small prickles of similar shape and coloration.

The color of the branches is between 146B and 137C sometimes heavily suffused especially under cooler weather conditions with between 183B and 187A. They bear some large prickles which are of similar size and shape to the large prickles on the major stems; prickle color is between 164C and 161A. The branches bear few small prickles of similar shape and coloration.

The color of the new shoots is between 146B and 137C often heavily suffused with between 183B and 187B. They bear some large prickles which are of similar size and shape to the large prickles on the major stems; prickle color is between 160A and 152B often moderately suffused with between 187B and 187C. The shoots bear few small prickles of similar shape and coloration and some stipitate glands.

I claim:

1. A new and distinct Grandiflora rose plant of the variety substantially as described and illustrated herein.

* * * * *

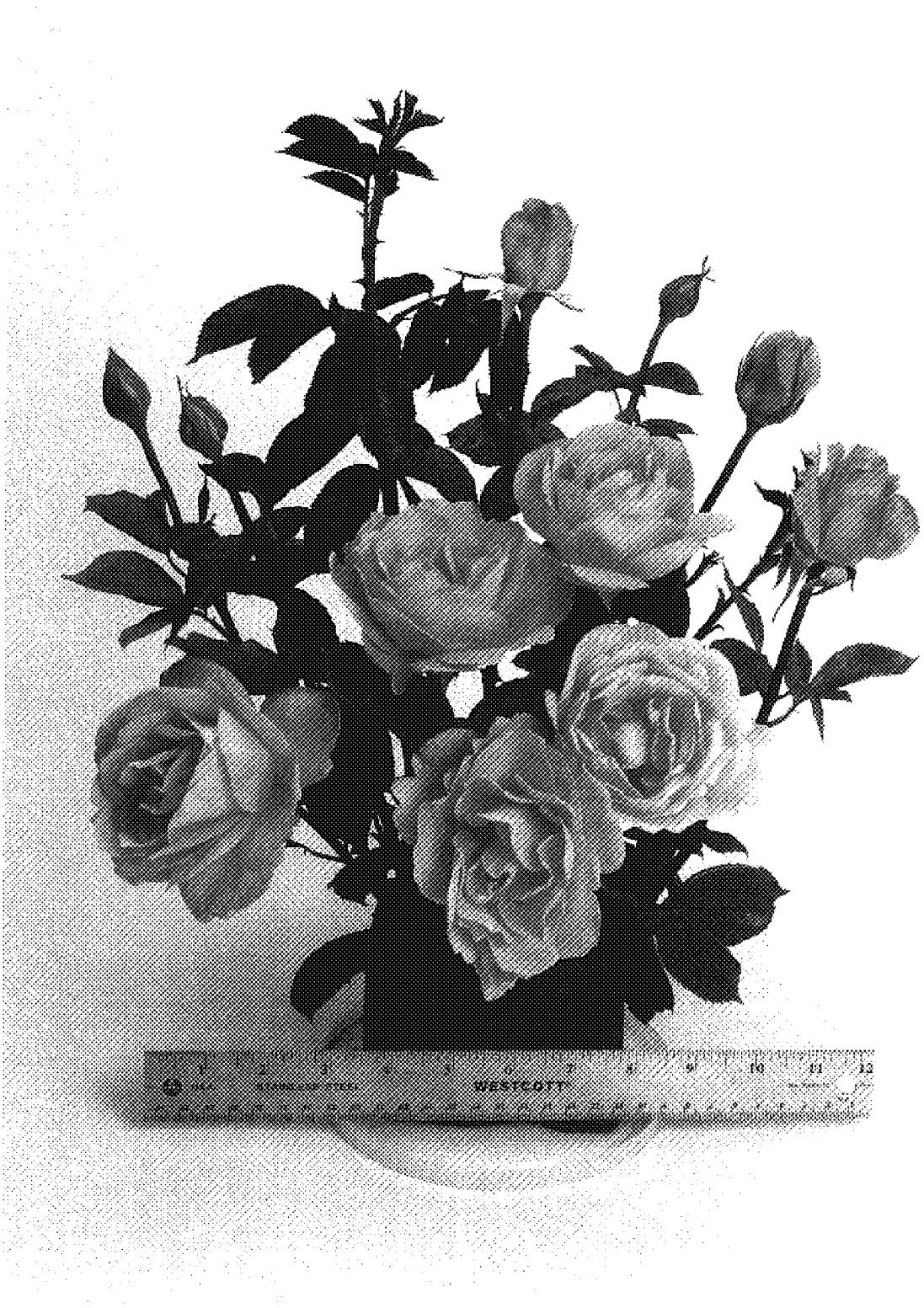
WESTCOTT